United States Patent
Anderson et al.

(10) Patent No.: US 11,419,646 B2
(45) Date of Patent: Aug. 23, 2022

(54) HAMMERTOE IMPLANT PROMOTING BONY IN-GROWTH

(71) Applicant: Biomet Manufacturing, LLC, Warsaw, IN (US)

(72) Inventors: David M. Anderson, Winona Lake, IN (US); Chad Westphal, Phoenix, AZ (US); Pierre Barouk, Bordeaux (FR)

(73) Assignee: Biomet Manufacturing, LLC, Warsaw, IN (US)

( * ) Notice: Subject to any disclaimer, the term of this patent is extended or adjusted under 35 U.S.C. 154(b) by 161 days.

(21) Appl. No.: 16/400,225

(22) Filed: May 1, 2019

(65) Prior Publication Data
US 2019/0254722 A1    Aug. 22, 2019

Related U.S. Application Data

(63) Continuation of application No. 15/367,932, filed on Dec. 2, 2016, now Pat. No. 10,321,940.
(Continued)

(51) Int. Cl.
*A61B 17/72* (2006.01)
*A61F 2/30* (2006.01)
*A61F 2/42* (2006.01)

(52) U.S. Cl.
CPC ...... *A61B 17/7233* (2013.01); *A61B 17/7291* (2013.01); *A61F 2/30771* (2013.01);
(Continued)

(58) Field of Classification Search
CPC .. A61B 17/7291; A61B 17/7233; A61B 17/72
See application file for complete search history.

(56) References Cited

U.S. PATENT DOCUMENTS 4,522,200 A * 6/1985 Stednitz ............. A61B 17/7291
                                                  606/63
6,127,597 A   10/2000 Beyar et al.
(Continued)

FOREIGN PATENT DOCUMENTS

EP        1905392 A1     4/2008
WO  WO-2008044011 A2 *  4/2008  ......... A61B 17/7225
(Continued)

OTHER PUBLICATIONS

"U.S. Appl. No. 15/367,932, Advisory Action dated Jul. 26, 2018", 3 pgs.
(Continued)

*Primary Examiner* — Julianna N Harvey
(74) *Attorney, Agent, or Firm* — Schwegman Lundberg & Woessner, P.A.

(57) ABSTRACT

Joint implants, such as joint implants used for placement in toes to treat hammertoe are described. More particularly, joint implants that include a proximal portion configured to be inserted into a first bone, a distal portion configured to be inserted into a second adjacent bone, and an elongated body positioned between the distal and distal portion is described. The elongated body can define a length and include at least one metal rod extending from the proximal portion to the distal portion and a porous mesh extending along at least a portion of the elongated body length. The porous mesh can be configured to allow for bony in-growth upon implantation, wherein the elongated body defines a generally square cross section and is configured to be inserted into drilled circular holes in the first and second bones. Methods of fusing two adjacent phalanges of a two are also described.

18 Claims, 6 Drawing Sheets

Related U.S. Application Data (60) Provisional application No. 62/262,494, filed on Dec. 3, 2015.

(52) U.S. Cl.
CPC ... *A61F 2/4225* (2013.01); *A61F 2002/30622* (2013.01); *A61F 2002/30914* (2013.01); *A61F 2002/4233* (2013.01)

(56) References Cited

U.S. PATENT DOCUMENTS

| | | | |
|---|---|---|---|
| 6,261,289 | B1 | 7/2001 | Levy |
| 6,319,255 | B1 * | 11/2001 | Grundei ................. A61B 17/70 606/246 |
| 10,321,940 | B2 | 6/2019 | Anderson et al. |
| 2006/0041262 | A1 | 2/2006 | Calvert et al. |
| 2008/0269745 | A1 | 10/2008 | Justin |
| 2009/0182336 | A1 * | 7/2009 | Brenzel ................. A61B 17/869 606/62 |
| 2010/0087821 | A1 * | 4/2010 | Trip ................... A61B 17/7233 606/63 |
| 2010/0094292 | A1 * | 4/2010 | Parrott ............... A61B 17/7283 606/62 |
| 2015/0073413 | A1 | 3/2015 | Palmer et al. |
| 2017/0156766 | A1 | 6/2017 | Anderson et al. |

FOREIGN PATENT DOCUMENTS

| | | | |
|---|---|---|---|
| WO | WO-2016044739 A1 * | 3/2016 | ......... A61B 17/7055 |
| WO | WO-2017096199 A1 | 6/2017 | |

OTHER PUBLICATIONS

"U.S. Appl. No. 15/367,932, Final Office Action dated May 9, 2018", 13 pgs.
"U.S. Appl. No. 15/367,932, Non Final Office Action dated Aug. 30, 2018", 18 pgs.
"U.S. Appl. No. 15/367,932, Non Final Office Action dated Nov. 24, 2017", 10 pgs.
"U.S. Appl. No. 15/367,932, Notice of Allowance dated Feb. 5, 2019", 7 pgs.
"U.S. Appl. No. 15/367,932, Response filed Oct. 31, 2017 to Restriction Requirement dated Oct. 4, 2017", 6 pgs.
"U.S. Appl. No. 15/367,932, Response filed Feb. 27, 2018 to Non Final Office Action dated Nov. 24, 2017", 9 pgs.
"U.S. Appl. No. 15/367,932, Response filed Jul. 9, 2018 to Final Office Action dated May 9, 2018", 12 pgs.
"U.S. Appl. No. 15/367,932, Response filed Aug. 9, 2018 to Advisory Action dated Jul. 26, 2018", 12 pgs.
"U.S. Appl. No. 15/367,932, Response filed Nov. 30, 2018 to Non Final Office action dated Aug. 30, 2018", 12 pgs.
"U.S. Appl. No. 15/367,932, Restriction Requirement dated Oct. 4, 2017", 6 pgs.
"European Application Serial No. 16813297.5, Response Filed Feb. 11, 2019 to Communication pursuant to Rules 161(2) and 162 EPC dated Aug. 1, 2018", 33 pgs.
"International Application Serial No. PCT/US2016/064673, International Preliminary Report on Patentability dated Jun. 14, 2018", 7 pgs.
"International Application Serial No. PCT/US2016/064673, International Search Report dated Mar. 9, 2017", 4 pgs.
"International Application Serial No. PCT/US2016/064673, Written Opinion dated Mar. 9, 2017", 5 pgs.
U.S. Appl. No. 15/367,932, filed Dec. 2, 2016, Hammertoe Implant Promoting Bony In-Growth.

\* cited by examiner

HAMMERTOE IMPLANT PROMOTING BONY IN-GROWTH

PRIORITY APPLICATIONS

This application is a continuation of U.S. patent application Ser. No. 15/367,932, filed Dec. 2, 2016, which claims the benefit of priority to U.S. Provisional Application Ser. No. 62/262,494, filed Dec. 3, 2015, the content of each of which is hereby incorporated by reference in its entirety.

BACKGROUND

Hammertoe is a well-known condition that consists of a contracture of one or both joints of the second, third, fourth or fifth toes. Most commonly the middle joint of the toe in question, the proximal interphalangeal (PIP) joint, is bent at an angle. In severe cases of hammertoe, surgery may be recommended. One such surgery is a tendon transfer procedure. Alternatively, hammertoes may be corrected using a joint arthroplasty (removing part of the bones on both sides of the PIP) or a joint fusion. In the case of a joint fusion, an intramedullary implant is placed into the end of the bones on the opposing sides of the joint and spans the joint. The goal is to fuse the two phalanges on opposing side of the joint where the contracture is occurring together.

OVERVIEW

The present inventors have recognized, among other things, that a problem to be solved can include addressing the fusion and rotational concerns of presently used hammertoe implants in fusion surgery. Presently used implants can suffer the drawback of ineffectively fixing rotation of the phalanges on the opposing sides of the joint, and not effectively promoting bone growth around the implant (which leads to effective fusion). The present subject matter can help provide a solution to this problem, such as by providing an implant with a proximal portion configured for insertion into a first bone and a distal portion configured for insertion into a second bone adjacent to the first bone. The implant further includes an elongated body extending between the proximal portion and the distal portion that defines an elongated body length. The elongated body includes at last one metal rod extending from the proximal portion to the distal portion and a porous mesh extending along at least a portion of the elongated body length. The porous mesh can allow for bony in-growth upon implantation, and the elongated body can define a generally square cross section and can be insertable into circular holes disposed in the first and second bones.

The present subject matter further provides a solution to the aforementioned problems by virtue of a method of fusing a first phalanx of a toe to a second phalanx of the toe. The method can include drilling a generally circular hole into the first phalanx; drilling a generally circular hole into the second phalanx; inserting a proximal end of an implant into the first bone, and advancing the implant until tabs positioned on the side of the implant body come into contact with the edge of the first phalanx or anchor within the circular hole in the first phalanx, the implant having a generally square cross-section and containing a metal rod and a porous metal material; and advancing the circular hole in the second phalanx over a distal end of the implant and over the elongated body of the implant until it is positioned proximate the first bone. The porous metal material of the implant promotes bony in-growth of both the first and second phalanges to the implant and aids in fusion.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present description is generally directed to bone implants that are capable of fusing two or more adjacent bones, and particularly to elongated bone implants that promote bony in-growth upon implantation. One exemplary use for such implants is in treating and addressing a hammertoe condition in patients.

Figure 1:
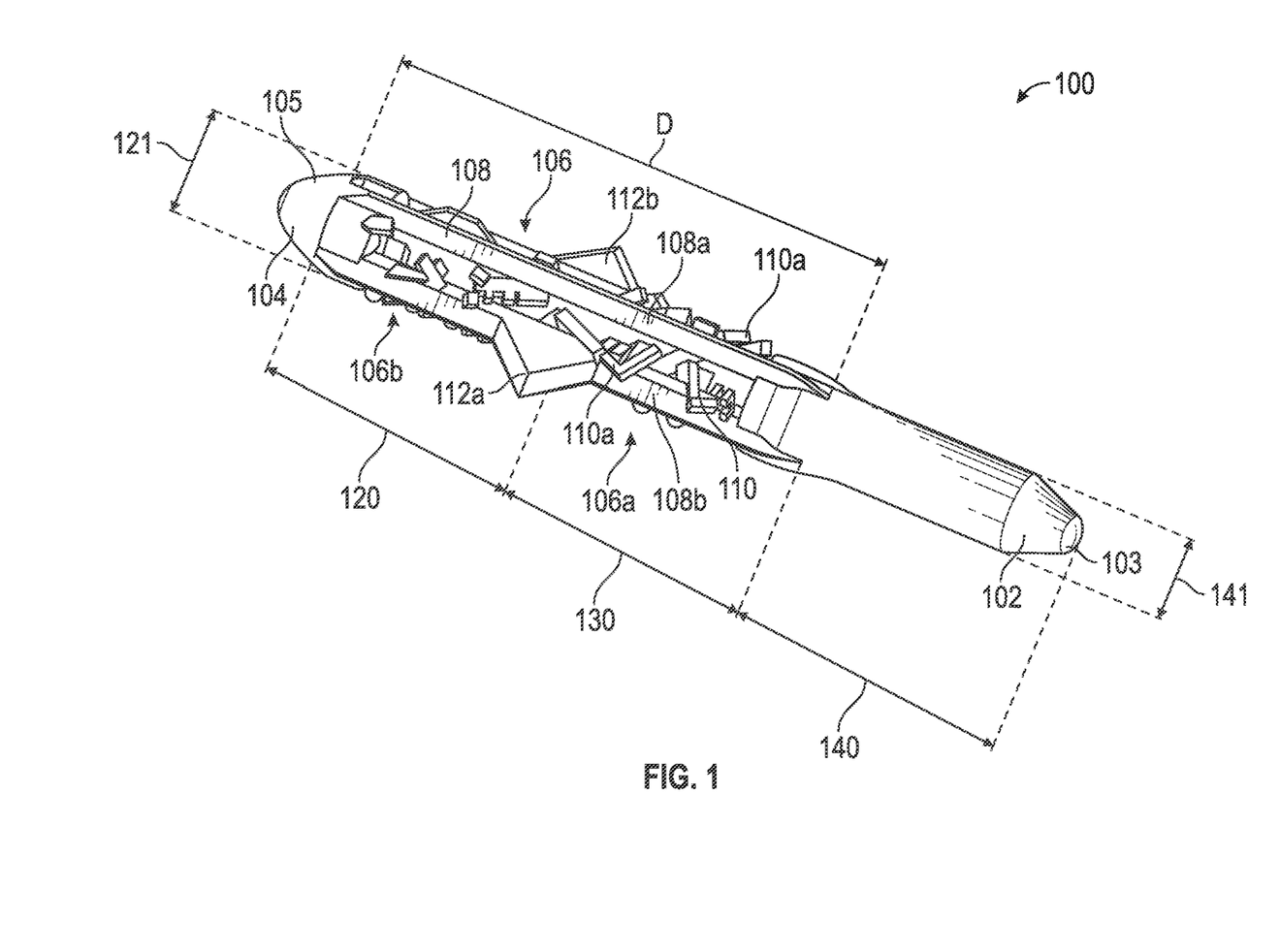
FIG. 1 provides a perspective view of an implant according to at least one example of the present description.
Figure 2A:
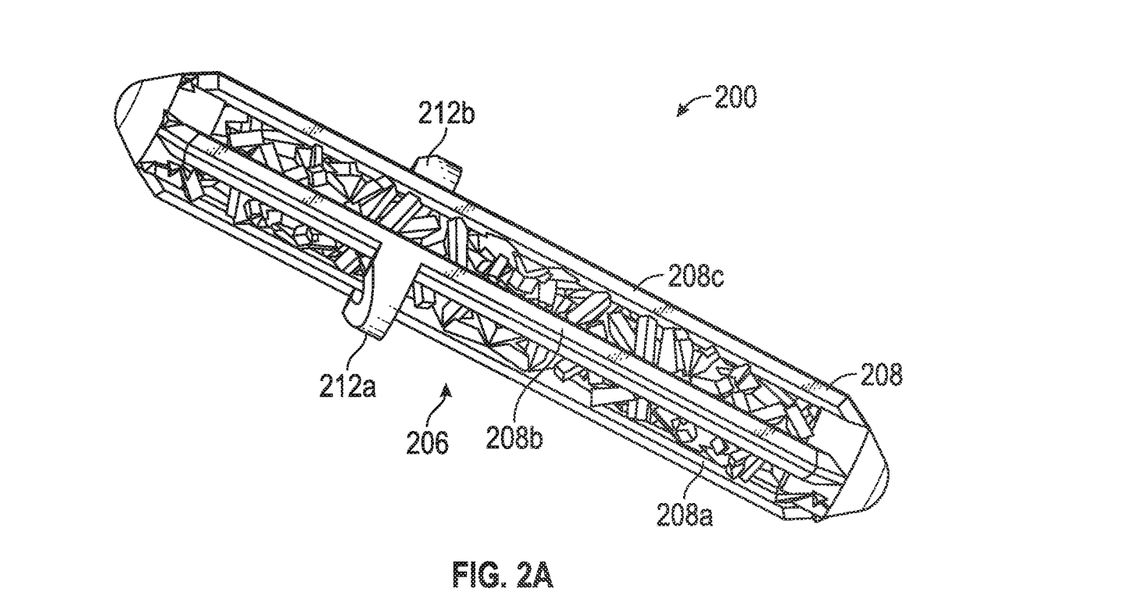
FIGS. 2A-2D provide a perspective view, top view, side view and end view, respectively, of an implant according to at last one example of the present description.
Figure 2B:
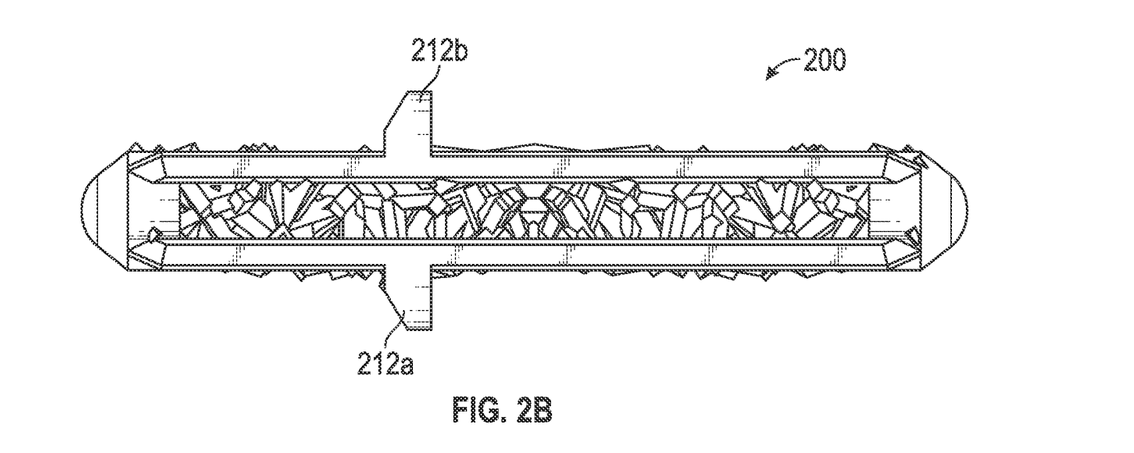
Figure 2C:
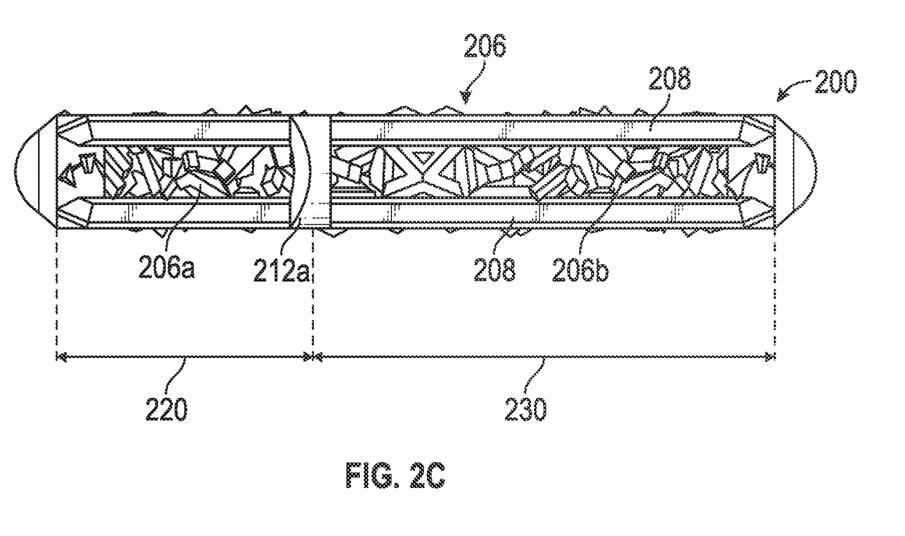
Figure 2D:
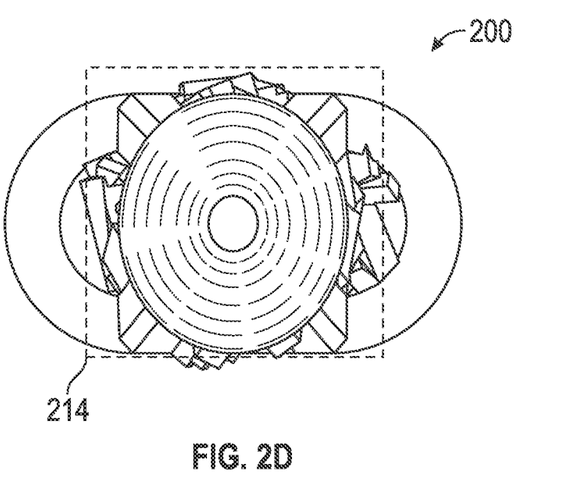

FIG. 1 provides a perspective view of joint implant 100. Joint implant 100 can include a proximal portion 102 that is insertable into a first bone and a distal portion 104 that is insertable into a second bone that is adjacent to the first bone. The proximal portion 102 and distal portion 104 can each include a rounded end (103 and 105, respectively). In one example, each of the ends 103 and 105 can be generally "bullet-shaped".

In one example, the first bone (into which the proximal portion 102 is configured to be inserted) can be a proximal phalanx of a toe and the second bone (into which the distal portion 104 is configured to be inserted) can be a middle phalanx of a toe. In such an example, the implant 100 can span the proximal interphalangeal (PIP) joint. Alternatively, the first bone can be the middle phalanx and the second bone can be the distal phalanx. In such an example, the implant 100 can span the distal interphalangeal (DIP) joint. Further, in yet another alternative example, the first bone can be the metatarsal adjacent to a toe and the second bone can be the adjacent proximal phalanx. Finally, the implant 100 can be used to span the interphalangeal joint of the hallux (or big toe).

Joint implant 100 can comprise an elongated body 106 that extends between the proximal portion 102 and distal portion 104. The elongated body 106 can define an elongated body length D. Elongated body 106 can include at least one metal rod 108 extending at least partway from the proximal portion 102 to the distal portion 104 along the length D. In one example, metal rod 108 can be titanium or a titanium alloy. The metal rod 108 can, in some examples, be integrally formed with the proximal portion 102 and distal portion 104 of the implant 100. In some examples, the proximal portion 102 and distal portion 104 can also be made up, at least in part, of titanium or a titanium alloy.

The elongated body 106 can further comprise a porous mesh 110 that extends along at a least a portion of the elongated body length D. The porous mesh 110 can allow for or facilitate bony in-growth upon implantation into the first and second bones. In one example, the porous mesh can be a porous titanium alloy mesh. One example of a titanium alloy that can be used for porous metal mesh is OsseoTi™ porous metal from Zimmer Biomet (Warsaw, Ind.). OsseoTi is made out of Ti6Al4V and has a porous structure that generally mimics the porous structure of human cancellous bone. It is highly biocompatible and has excellent corrosion resistance. Additionally or alternatively, the porous mesh can be Trabecular Metal™, also from Zimmer Biomet. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. The porous mesh can comprise one or more of a variety of biocompatible metals such as, but not limited to, titanium, titanium alloys, cobalt chromium, cobalt chromium molybdenum, tantalum, tantalum alloys, niobium, or alloys of tantalum and niobium with one another or with other metals, and the like. The porous mesh can be particularly suited for contacting bone and/or soft tissue and can be useful as a bone substitute, implant, or implant component that can be receptive to cell and tissue ingrowth, for example, by allowing and promoting bony tissue or other tissue growth into the porous structure over time to enhance fixation (e.g., osseointegration) between the structure and surrounding bodily structures.

The elongated body 106 can also define a generally rectangular and, more particularly, generally square cross section. The cross section of elongated body 106 can be configured for insertion into circular holes disposed in the first and second bones. The rectangular or square cross-section of the implant in opposition to the circular cross-section of the drilled bores can facilitate creation of a static force that can aid in creating an interference fit of the implant in the hole of the bone and can oppose or prohibit rotational movement of the implant upon implantation. The elongated body 106 can comprise a first elongated body portion 106a that can have a first length 120 and a second a second elongated body portion 106b that can have a second length 130. The first length 120 and the second length 130 can be equal or different. The elongate body 106 can further comprise a first diameter 121. The implant 100 can comprise a proximal portion 102 (or a distal portion 104) having a third length 140. The portion of the proximal portion 102 (or the distal portion 104) corresponding to the third length 140 can have a second diameter 141 that can be less than the first diameter 121 of the elongate body 106. The second diameter 141 can be smaller than the first diameter 121 to facilitate introduction into or through a narrow section of bone to further enhance stability and fixation of the implant 100.

The joint implant 100 can optionally further include first and second tabs 112a and 112b. The first and second tabs 112a and 112b can be configured to prohibit the proximal portion 102 from being implanted beyond a given distance into the first bone. In one example, the first tab 112a and second tab 112b can each have a generally triangular profile (as illustrated in FIG. 1). However, other appropriate profile shapes are also contemplated, such as hemispheric (see FIGS. 2A-D), and the like.

As illustrated in FIG. 1, in some examples, the joint implant 100 can include a plurality of metal rods 108, (see, e.g., rods 108a and 108b). The plurality of metal rods 108 can define a perimeter along the length D of the elongated body 106. The metal rods 108a, 108b can correspond to the overall cross-sectional profile (e.g., can be spaced such that they form a generally square cross-section). Although only two rods 108a, 108b are visible in FIG. 1, the example can include a total of four rods 108 equally spaced around the perimeter of the cross section of the elongated body 106. In other examples, any number of rods 108 can be used, such as three rods, five rods, six rods, or more.

As further illustrated, mesh 110 can, in some examples, be at least partially positioned between the plurality of metal rods 108 along at least a portion of the elongated body length D. In some examples at least a portion of the mesh (see, e.g., portions of mesh 110a) can extend outside of the perimeter defined by the metal rods. A portion of mesh 110 extending beyond the perimeter created by rods 108 can enable the mesh 110 to contact the surrounding bone after implantation, which can aid in both promoting bony in-growth and in creating a static force to secure the implant 100. Additionally or alternatively, the mesh 110 does not extend outside of the perimeter defined by the metal rods 108 but can still contact surrounding bone after implantation.

As illustrated in FIGS. 2A-2D, implant 200, like implant 100, can comprise a metal rod 208, and can further comprise a plurality of metal rods (e.g., 208a, 208b, 208c). The first tab 212a and second tab 212b can have a generally hemispheric profile; however, alternative profile shapes are also contemplated. In one example, a cross-section 214 of the implant along the elongated body 206 can be generally rectangular, or more particularly, generally square. The elongated body 206 can comprise a first elongated body portion 206a that can have a first length 220 and a second a second elongated body portion 206b that can have a second length 230. The first length 220 and the second length 230 can be equal or different.

Figure 3:
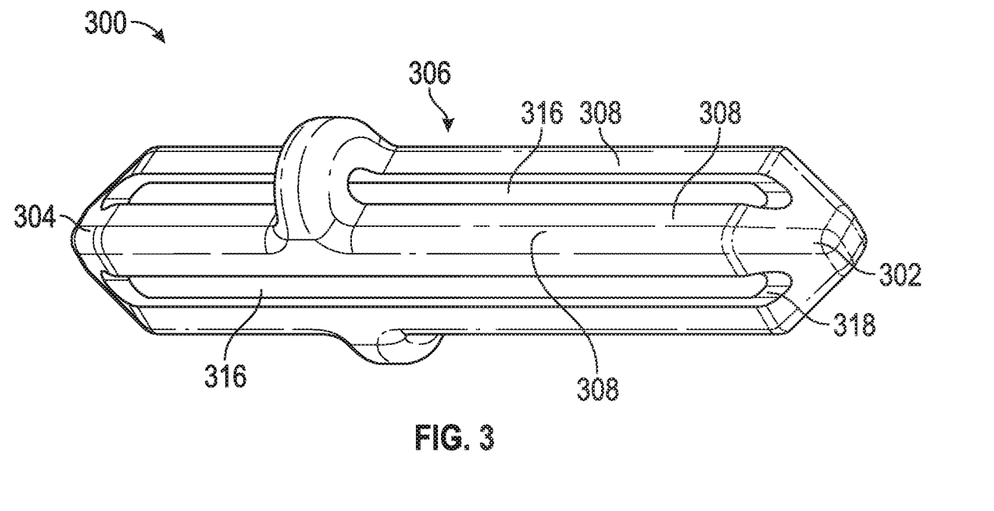
FIG. 3 provides a perspective view of an implant according to at least one example of the present description.

As illustrated in FIG. 3, implant 300 can comprise at least one metal rod 308. The metal rod 308 can further comprise a hollow core disposed in extending at least part of the length of the metal rod 308. Additionally or alternatively, the metal rod 308 can further include a plurality of voids 316. Voids 316 can generally run from proximal end 302 to the distal end 304 along elongated body 306. Additionally or alternatively, the voids 316 can be circular or any other appropriate shape and can be positioned at various points along the length and at various points around the perimeter of the body 306. The voids 316 extend from an exterior surface 318 of rod 308 to the hollow core. Mesh can be positioned within the hollow core such that voids 316 provide a plurality of small openings at which the mesh can come directly into contact with bodily material. Joint implant 300 can provide for more limited openings and surface area where bony in-growth can occur compared to previous examples which can be desirable in some cases.

Figure 4:
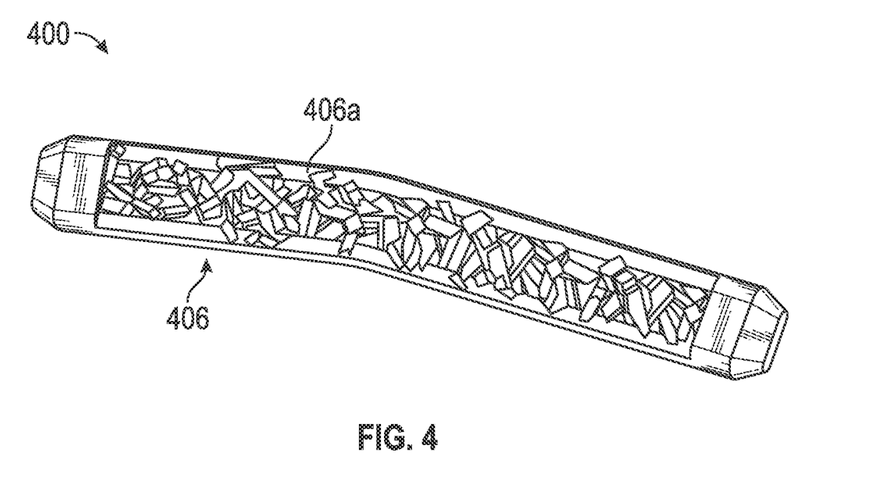
FIG. 4 provides a side view of an implant according to at least one example of the present description.

As illustrated in FIGS. 1-3, implants described herein can generally extend along a common axis along the length D of elongated body 106 (or 206, 306). However, other configurations are possible. In some examples illustrated in FIG. 4, especially in applications for hammertoe treatment, it can be desirable to provide at least a slight angle in the implant 400 that can correspond to the joint position between the two bones where fusion will occur. Implant 400 can have a point 406a along the elongated body 406 where the axis of the implant is altered.

Figure 5A:
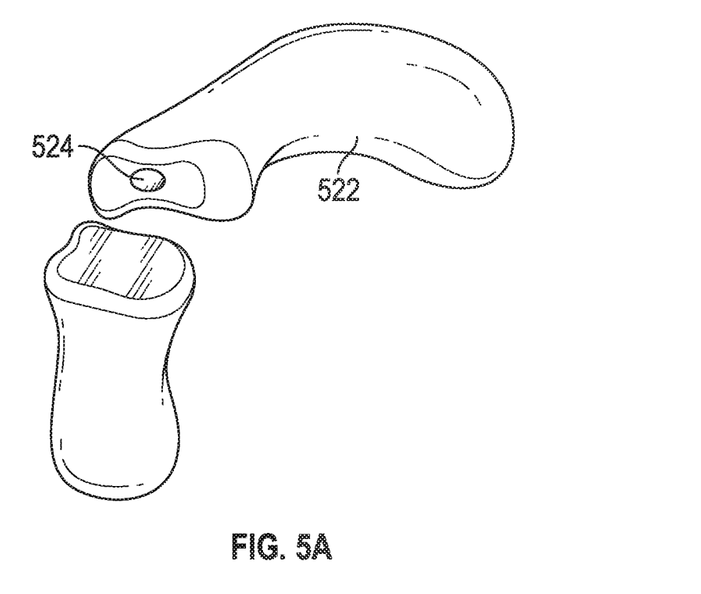
FIGS. 5A-5D provides a number of views of steps in a method of fusing a first phalanx of a toe to a second phalanx of the toe, according to at least one example of the present description.
Figure 5B:
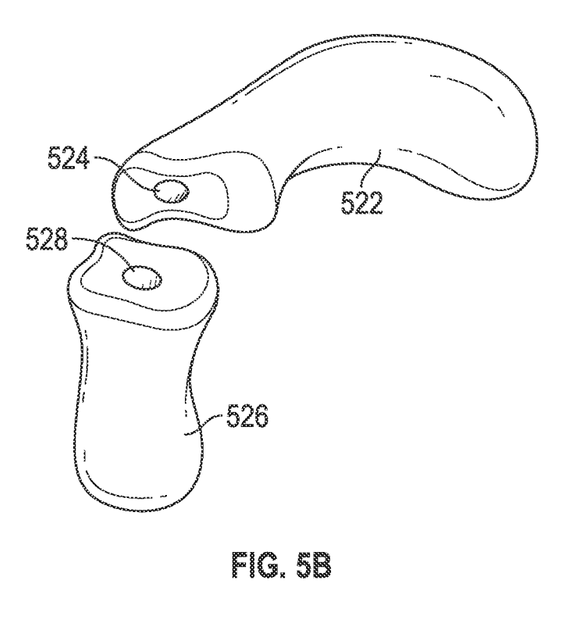

A method of fusing two bones, for example, a first phalanx of a toe and a second phalanx of the toe, is also contemplated. FIGS. 5A-5D illustrate one exemplary method. As illustrated in FIG. 5A, the method can comprise drilling a generally circular hole 524 into the first phalanx 522. As illustrated in FIG. 5B, the method can further comprise drilling a generally circular hole 528 into the second phalanx 526 of the same toe. Next, a proximal portion 102 and a portion of elongated body 106 of an implant 100 can be inserted into the first bone 522, and the implant can be advanced until tabs 112 positioned on the side of the implant body come into contact with the edge of the first phalanx 522 or anchor within the circular hole 524 in the first phalanx. The implant can have a generally square cross-section and can contain a metal rod and a porous metal material (as provided in implants 100, 200, 300 and 400 described above). In at least one example, the interface of the circular holes in the first and second phalanges and the generally rectangular cross-section of the implant can aid in securing the implant and minimizing or eliminating rotation between the first and second phalanges.

Figure 5C:
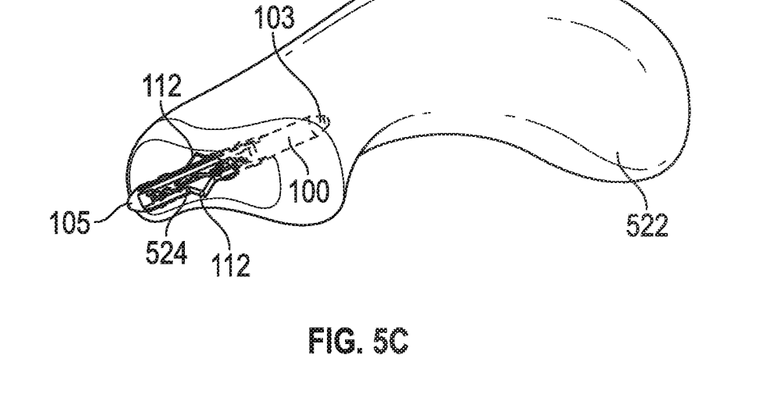
Figure 5D:
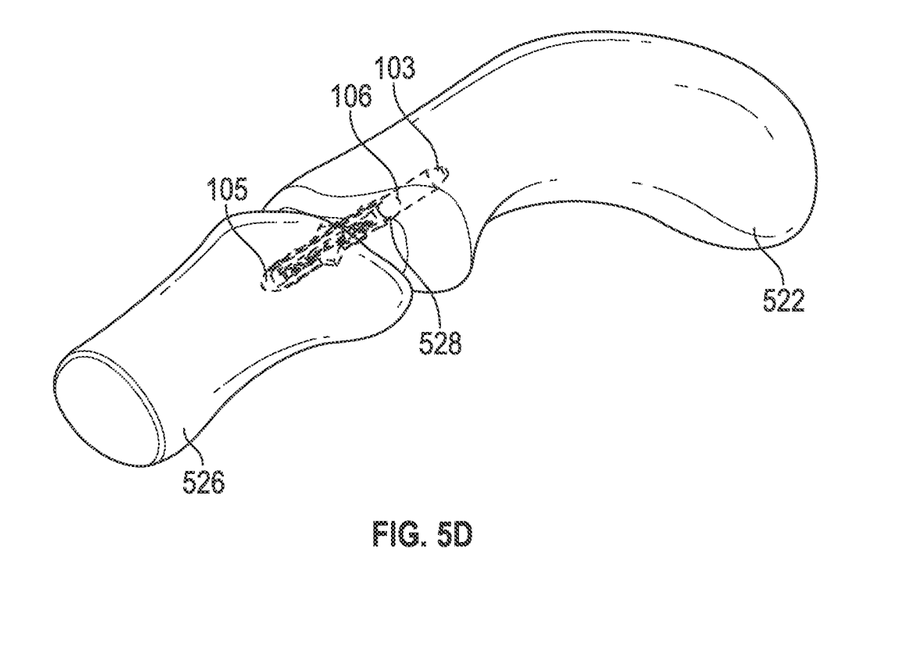

The method can further comprise advancing the circular hole 528 in the second phalanx 526 over a distal portion 104 of the implant 100 until it is positioned proximate the first bone 522. The porous metal material of the implant can promote bony in-growth of both the first and second phalanges into the implant, which can aid in fusion.

In at least one example, the first phalanx in the method described above can be a proximal phalanx of a given toe and the second phalanx can be a middle phalanx of the given toe. Alternatively, the first phalanx can be a middle phalanx and the second phalanx can be a distal phalanx.

Various Notes & Examples

Example 1 can include a joint implant, such as a joint implant that can include a proximal portion insertable into a hole disposed in a first bone, a distal portion insertable into a hole disposed in a second bone, the second bone positioned adjacent to the first bone, and an elongated body positioned between the proximal portion and the distal portion. The elongated body defines an elongated body length. The elongated body can comprise at least one metal rod extending from the proximal portion to the distal portion and a porous mesh extending along at least a portion of the elongated body length. The elongated body can define a generally rectangular cross section.

Example 2 can include, or can optionally be combined with the subject matter of Example 1, to optionally include the first bone comprising a proximal phalanx of a toe and the second bone comprising a middle phalanx of a toe.

Example 3 can include, or can optionally be combined with the subject matter of Example 1 to optionally include the first bone comprising a middle phalanx of a toe and the second bone comprising a distal phalanx of a toe.

Example 4 can include, or can optionally be combined with the subject matter of Example 1 to optionally include the first bone comprising a metatarsal and the second bone comprising a proximal phalanx.

Example 5 can include, or can optionally be combined with the subject matter of one or any combination of Examples 1-4 to optionally include the proximal portion and the distal portion each include a rounded end.

Example 6 can include, or can optionally be combined with the subject matter of one or any combination of Examples 1-5 to optionally include the porous mesh includes a porous titanium alloy mesh.

Example 7 can include, or can optionally be combined with the subject matter of one or any combination of Examples 1-6 to optionally include the metal rod comprises titanium.

Example 8 can include, or can optionally be combined with the subject matter of one or any combination of Examples 1-7 to optionally include first and second tabs extending outwardly from the elongated body, the first and second tabs positioned on opposing sides of the elongated body.

Example 9 can include, or can optionally be combined with the subject matter of one or any combination of Examples 1-8 to optionally include first and second tabs configured to prohibit the proximal portion from being implanted beyond a given distance into the first or second bone.

Example 10 can include, or can optionally be combined with the subject matter of one or any combination of Examples 1-9 to optionally include first and second tabs having a generally hemispheric profile.

Example 11 can include, or can optionally be combined with the subject matter of one or any combination of Examples 1-9 to optionally include first and second tabs have a generally triangular profile.

Example 12 can include, or can optionally be combined with the subject matter of one or any combination of Examples 1-11 to optionally include the at least one metal rod comprises a plurality of metal rods which define a perimeter along the length of the elongated body and corresponding to the overall cross-sectional profile.

Example 13 can include, or can optionally be combined with the subject matter of one or any combination of Examples 1-12 to optionally include the porous mesh positioned generally between the plurality of metal rods along at least a portion of the elongated body length.

Example 14 can include, or can optionally be combined with the subject matter of one or any combination of Examples 1-13 to optionally include wherein at least a portion of the porous mesh extends outside of the perimeter defined by the metal rods to enable contact with surrounding bone after implantation.

Example 15 can include, or can optionally be combined with the subject matter of one or any combination of Examples 1-13 to optionally include wherein at least a portion of the porous mesh remains within the perimeter defined by the metal rods.

Example 16 can include, or can optionally be combined with the subject matter of one or any combination of Examples 1-15 to optionally include at least one metal rod includes a hollow core and a plurality of voids extending from an exterior surface of the rod to the hollow core.

Example 17 can include, or can optionally be combined with the subject matter of one or any combination of Examples 1-16 to optionally include the distal and distal portions being integrally formed with the at least one metal rod.

Example 18 can include, or can optionally be combined with the subject matter of one or any combination of Examples 1-17 to optionally include that the distal and distal portions comprise titanium.

Example 19 can include, or can optionally be combined with the subject matter of one or any combination of Examples 1-18 to optionally include wherein the elongated body defines a generally square cross section.

Example 20 can include a joint implant comprising a proximal portion that can be insertable into a hole disposed in a first bone, a distal portion that can be insertable into a hole disposed in a second bone, the second bone positioned adjacent to the first bone, and an elongated body extending between the proximal portion and the distal portion and defining an elongated body length. The elongated body can comprise a plurality of metal rods that can extend from the proximal portion to the distal portion and a porous mesh that can extend along at least a portion of the elongated body length. The elongated body can define a generally rectangular cross section. The plurality of metal rods, the proximal portion, and the distal portion can be integrally formed.

Example 21 can include a method of fusing a first phalanx of a toe to a second phalanx of the toe. The method can include drilling a generally circular hole into the first phalanx; drilling a generally circular hole into the second phalanx; inserting a proximal end of an implant into the first bone, and advancing the implant until tabs positioned on the side of the implant body come into contact with the edge of the first phalanx or anchor within the circular hole in the first phalanx, the implant having a generally square cross-section and containing a metal rod and a porous metal material; and advancing the circular hole in the second phalanx over a distal end of the implant and over the elongated body of the implant until it is positioned proximate the first bone. The porous metal material of the implant promotes bony ingrowth of both the first and second phalanges to the implant and aids in fusion.

Example 22 can include, or can optionally be combined with the subject matter of Example 22 to optionally include the interface of the circular holes in the first and second phalanges and the general rectangular cross-section of the implant aiding in securing the implant and minimizes rotation between the first and second phalanges.

Example 23 can include, or can optionally be combined with the subject matter of one or any combination of Examples 21-22 to optionally include the first phalanx being a proximal phalanx and the second phalanx being a middle phalanx.

Each of these non-limiting examples can stand on its own, or can be combined in various permutations or combinations with one or more of the other examples. While portions of the description reference, specifically, application directed towards hammertoe and implantation into the phalanges of the toe and/or the metatarsal, as well as methods of fusing toe bones, one of skill in the art will understand that the presently described implants and methods of fusion can be used, e.g., with the bones of the hand, or with other bones throughout the body.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A joint implant extending along a longitudinal axis, comprising:
   a proximal portion insertable into a drilled hole disposed in a first bone, the proximal portion having a solid proximal end, the solid proximal end having a proximal cross-sectional size in a plane perpendicular to the longitudinal axis;
   a distal portion insertable into a drilled hole disposed in a second bone, the second bone positioned adjacent to the first bone, the distal portion having a solid distal end, the solid distal end having a distal cross-sectional size in the plane perpendicular to the longitudinal axis;
   an elongated body extending along the longitudinal axis between the proximal portion and the distal portion, the elongated body defining a hollow interior and an exterior surface, the elongated body including a first metal rod and a second metal rod that each extend substantially along an entire length of the elongated body from the proximal portion to the distal portion, a separation between the first metal rod and the second metal rod being less than the proximal cross-sectional size and less than the distal cross-sectional size, the separation extending in a plane perpendicular to the longitudinal axis proximate a midpoint of the elongated body; and a metallic porous structure positioned within a portion of the hollow interior of the elongated body and projecting outwardly from the exterior surface of the elongated body such that a plurality of voids created by the metallic porous structure extend from an exterior of the elongated body to the hollow interior of the elongated body.

2. The joint implant of claim 1, further comprising a first tab extending outwardly from the elongated body, the first tab configured to prohibit the proximal portion from being implanted beyond a specified distance into the drilled hole in the first bone.

3. The joint implant of claim 2, wherein a spacing between the first tab and the proximal portion differs from a spacing between the first tab and the distal portion.

4. The joint implant of claim 2, further comprising a second tab extending outwardly from the elongated body, the second tab being positioned on an opposite side of the elongated body from the first tab.

5. The joint implant of claim 4, wherein:
a spacing between the first tab and the proximal portion equals a spacing between the second tab and the proximal portion; and
a spacing between the first tab and the distal portion equals a spacing between the second tab and the distal portion.

6. The joint implant of claim 4, wherein the first tab and the second tab each have a generally hemispheric profile.

7. The joint implant of claim 4, wherein the first tab and the second tab each have a generally triangular profile.

8. The joint implant of claim 1, wherein the first metal rod is formed integrally with the proximal portion and the distal portion.

9. The joint implant of claim 1, further comprising a plurality of metal rods that extend substantially along the entire length of the elongated body from the proximal portion to the distal portion, the plurality of metal rods including the first metal rod and the second metal rod.

10. The joint implant of claim 9, wherein the cross-sectional profile of the elongated body, taken in a plane orthogonal to a longitudinal axis of the elongated body, is generally rectangular.

11. The joint implant of claim 10, wherein the cross-sectional profile of the elongated body, taken in a plane orthogonal to a longitudinal axis of the elongated body, is generally square.

12. The joint implant of claim 9, wherein the plurality of metal rods define a perimeter along a length of the elongated body and correspond to a cross-sectional profile of the elongated body.

13. The joint implant of claim 12, wherein the metallic porous structure is positioned generally between the plurality of metal rods along at least a portion of the length of the elongated body.

14. The joint implant of claim 13, wherein at least a portion of the metallic porous structure extends outside of the perimeter defined by the metal rods.

15. The joint implant of claim 13, wherein at least a portion of the metallic porous structure remains within the perimeter defined by the metal rods.

16. The joint implant of claim 1, wherein:
the solid proximal end of the proximal portion is rounded to ease insertion of the proximal portion into the first bone; and
the solid distal end of the distal portion is rounded to ease insertion of the distal portion into the second bone.

17. The joint implant of claim 1; wherein:
the solid proximal end of the proximal portion is shaped to ease insertion of the proximal portion into the first bone; and
the solid distal end of the distal portion is shaped to ease insertion of the distal portion into the second bone.

18. A joint implant extending along a longitudinal axis, comprising:
a proximal portion insertable into a drilled hole disposed in a first bone, the proximal portion having a solid proximal end that is shaped to ease insertion of the proximal portion into the first bone, the solid proximal end having a proximal cross-sectional size in a plane perpendicular to the longitudinal axis;
a distal portion insertable into a drilled hole disposed in a second bone, the second bone positioned adjacent to the first bone, the distal portion having a solid distal end that is shaped to ease insertion of the distal portion into the second bone, the solid distal end having a distal cross-sectional size in the plane perpendicular to the longitudinal axis;
an elongated body extending along the longitudinal axis between the proximal portion and the distal portion, the elongated body defining a hollow interior and an exterior surface, the elongated body being generally rectangular in a cross-section taken orthogonal to a longitudinal axis of the elongated body, the elongated body including a plurality of metal rods that extend substantially along an entire length of the elongated body from the proximal portion to the distal portion, the plurality of metal rods being integrally formed with the proximal portion and the distal portion, a separation between two of the plurality of metal rods being less than the proximal cross-sectional size and less than the distal cross-sectional size, the separation extending in a plane perpendicular to the longitudinal axis proximate a midpoint of the elongated body; and
a porous titanium alloy structured to mimic a porous structure of human cancellous bone, the porous titanium alloy being positioned within a portion of the hollow interior of the elongated body and projecting outwardly from the exterior surface of the elongated body such that a plurality of voids created by the porous titanium alloy extend from an exterior of the elongated body to the hollow interior of the elongated body.

* * * * *

UNITED STATES PATENT AND TRADEMARK OFFICE
CERTIFICATE OF CORRECTION

| | | |
|---|---|---|
| PATENT NO. | : 11,419,646 B2 | |
| APPLICATION NO. | : 16/400225 | |
| DATED | : August 23, 2022 | |
| INVENTOR(S) | : Anderson et al. | |

It is certified that error appears in the above-identified patent and that said Letters Patent is hereby corrected as shown below:

In the Claims

In Column 10, Line 13, in Claim 17, delete "1;" and insert --1,-- therefor

Signed and Sealed this
First Day of November, 2022

*Katherine Kelly Vidal*

Katherine Kelly Vidal
*Director of the United States Patent and Trademark Office*